United States Patent
Busch et al.

(10) Patent No.: US 12,257,062 B2
(45) Date of Patent: Mar. 25, 2025

(54) SYSTEM AND PROCESS FOR COMPUTERIZED SCREENING AND MONITORING FOR COGNITIVE CHARACTERISTICS

(71) Applicant: The Cleveland Clinic Foundation, Cleveland, OH (US)

(72) Inventors: Robyn M. Busch, Richmond Heights, OH (US); Darlene P. Floden, University Heights, OH (US)

(73) Assignee: The Cleveland Clinic Foundation, Cleveland, OH (US)

(*) Notice: Subject to any disclaimer, the term of this patent is extended or adjusted under 35 U.S.C. 154(b) by 0 days.

(21) Appl. No.: 18/084,607

(22) Filed: Dec. 20, 2022

(65) Prior Publication Data
US 2023/0190176 A1 Jun. 22, 2023

Related U.S. Application Data

(60) Provisional application No. 63/292,253, filed on Dec. 21, 2021.

(51) Int. Cl.
*A61B 5/00* (2006.01)
*G16H 10/20* (2018.01)
*G16H 10/60* (2018.01)

(52) U.S. Cl.
CPC .......... *A61B 5/4064* (2013.01); *A61B 5/4076* (2013.01); *G16H 10/20* (2018.01); *G16H 10/60* (2018.01)

(58) Field of Classification Search
None
See application file for complete search history.

*Primary Examiner* — Kesha Frisby
(74) *Attorney, Agent, or Firm* — BakerHostetler

(57) ABSTRACT

A method and device includes generating and displaying a first set of objects and a second set of objects; displaying a first object belonging to either the first set of objects or the second set of objects; receiving a first response of whether the first object belongs to the first set of objects or the second set of objects; determining whether the first response correctly identifies a set of objects to which the first object belongs; displaying a second object from either the first set of objects or the second set of objects; receiving a second response of whether the first object belongs to the first set of objects or the second set of objects; determining whether the second response correctly identifies the set of objects to which the second object belongs; and applying an algorithm to determine a probability of a cognitive characteristic.

24 Claims, 5 Drawing Sheets

SYSTEM AND PROCESS FOR COMPUTERIZED SCREENING AND MONITORING FOR COGNITIVE CHARACTERISTICS

CROSS REFERENCE TO RELATED APPLICATIONS

This application claims the benefit of U.S. Provisional Application No. 63/292,253, filed Dec. 21, 2021, the entirety of which is incorporated by reference herein.

TECHNICAL FIELD

The disclosure is directed to a system for computerized screening and monitoring for cognitive characteristics. The disclosure is further directed to a process for computerized screening and monitoring for cognitive characteristics. In aspects, the disclosure relates to the field of cognitive assessments for use as screening tools for cognitive impairment. In aspects, the disclosure provides a computerized, patient-administered cognitive assessment that integrates into electronic medical records systems and provides clinicians with patient-provided cognitive data for aiding in clinical decision-making.

BACKGROUND

Adult cognitive testing or screening is used to evaluate problems or potential problems with a patient's mental function, or how the brain processes thoughts. Cognitive tests often involve answering simple questions and performing simple tests. Current cognitive assessments are limited by patient access. Generally, clinicians are only able to obtain cognitive testing data from patients in a clinical setting, which can reduce the access to meaningful data points. Furthermore, current assessments are limited in their predictive power by how comparative data is integrated.

Accordingly, there is a need for improved tools for assessing cognitive function in adults that integrates the depth of cognitive neuropsychological research and data available to clinicians while also providing an interface that is easily accessible to patients. The disclosure addresses this need as well as others.

SUMMARY

The foregoing needs are met, to a great extent, by the disclosure, wherein in one aspect a system and process for computerized screening and monitoring for cognitive characteristics are provided.

In one general aspect, a computer-implemented method includes generating a first set of objects and a second set of objects with a computing device. The computer-implemented method in addition includes displaying with the computing device the first set of objects to the patient individually, each for a period of time. The computer-implemented method moreover includes after all items in the first set have been presented, displaying with the computing device a first object belonging to either the first set of objects or the second set of objects. The computer-implemented method also includes receiving with the computing device a first response of whether the first object belongs to the first set of objects or the second set of objects. The computer-implemented method further includes determining with the computing device whether the first response correctly identifies a set of objects to which the first object belongs. The computer-implemented method in addition includes displaying with the computing device a second object from either the first set of objects or the second set of objects. The computer-implemented method moreover includes receiving with the computing device a second response of whether the first object belongs to the first set of objects or the second set of objects. The computer-implemented method also includes determining with the computing device whether the second response correctly identifies the set of objects to which the second object belongs. The computer-implemented method further includes applying with the computing device an algorithm to determine a probability of a cognitive characteristic based on a number of correct responses. The computer-implemented method in addition includes outputting with the computing device the probability of the cognitive characteristic.

In one general aspect, a device includes instructions for generating a first set of objects and a second set of objects with a computing device. The device in addition includes instructions for displaying with the computing device the first set of objects to the patient individually, each for a period of time. The device moreover includes instructions for after all items in the first set have been presented, displaying with the computing device a first object belonging to either the first set of objects or the second set of objects. The device also includes instructions for receiving with the computing device a first response of whether the first object belongs to the first set of objects or the second set of objects. The device further includes instructions for determining with the computing device whether the first response correctly identifies a set of objects to which the first object belongs. The device in addition includes instructions for displaying with the computing device a second object from either the first set of objects or the second set of objects. The device moreover includes instructions for receiving with the computing device a second response of whether the first object belongs to the first set of objects or the second set of objects. The device also includes instructions for determining with the computing device whether the second response correctly identifies the set of objects to which the second object belongs. The device further includes instructions for applying with the computing device an algorithm to determine a probability of a cognitive characteristic based on a number of correct responses. The device in addition includes instructions for outputting with the computing device the probability of the cognitive characteristic.

In one general aspect, the computing device includes at least one processor configured to generate a first set of objects and a second set of objects. The computing device in addition includes the at least one processor configured to display on a display device the first set of objects to the patient individually, each for a period of time. The computing device moreover includes the at least one processor configured to, after all items in the first set have been presented, display on the display device a first object belonging to either the first set of objects or the second set of objects. The computing device also includes the at least one processor configured to receive a first response of whether the first object belongs to the first set of objects or the second set of objects. The computing device further includes the at least one processor configured to determine whether the first response correctly identifies a set of objects to which the first object belongs. The computing device in addition includes the at least one processor configured to display on the display device a second object from either the first set of objects or the second set of objects. The computing device moreover includes the at least one processor configured to receive a second response of whether the first object belongs to the first set of objects or the second set of objects. The computing device also includes the at least one processor configured to determine whether the second response correctly identifies the set of objects to which the second object belongs. The computing device further includes the at least one processor configured to implement an algorithm to determine a probability of a cognitive characteristic based on a number of correct responses. The computing device in addition includes the at least one processor configured to output the probability of the cognitive characteristic.

There has thus been outlined, rather broadly, certain aspects of the disclosure in order that the detailed description thereof herein may be better understood, and in order that the present contribution to the art may be better appreciated. There are, of course, additional aspects of the disclosure that will be described below and which will form the subject matter of the claims appended hereto.

In this respect, before explaining at least one aspect of the disclosure in detail, it is to be understood that the disclosure is not limited in its application to the details of construction and to the arrangements of the components set forth in the following description or illustrated in the drawings. The disclosure is capable of aspects in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the disclosure. It is important, therefore, that the claims be regarded as including such equivalent constructions insofar as they do not depart from the spirit and scope of the disclosure.

DETAILED DESCRIPTION OF ILLUSTRATIVE EMBODIMENTS

Figure 1:
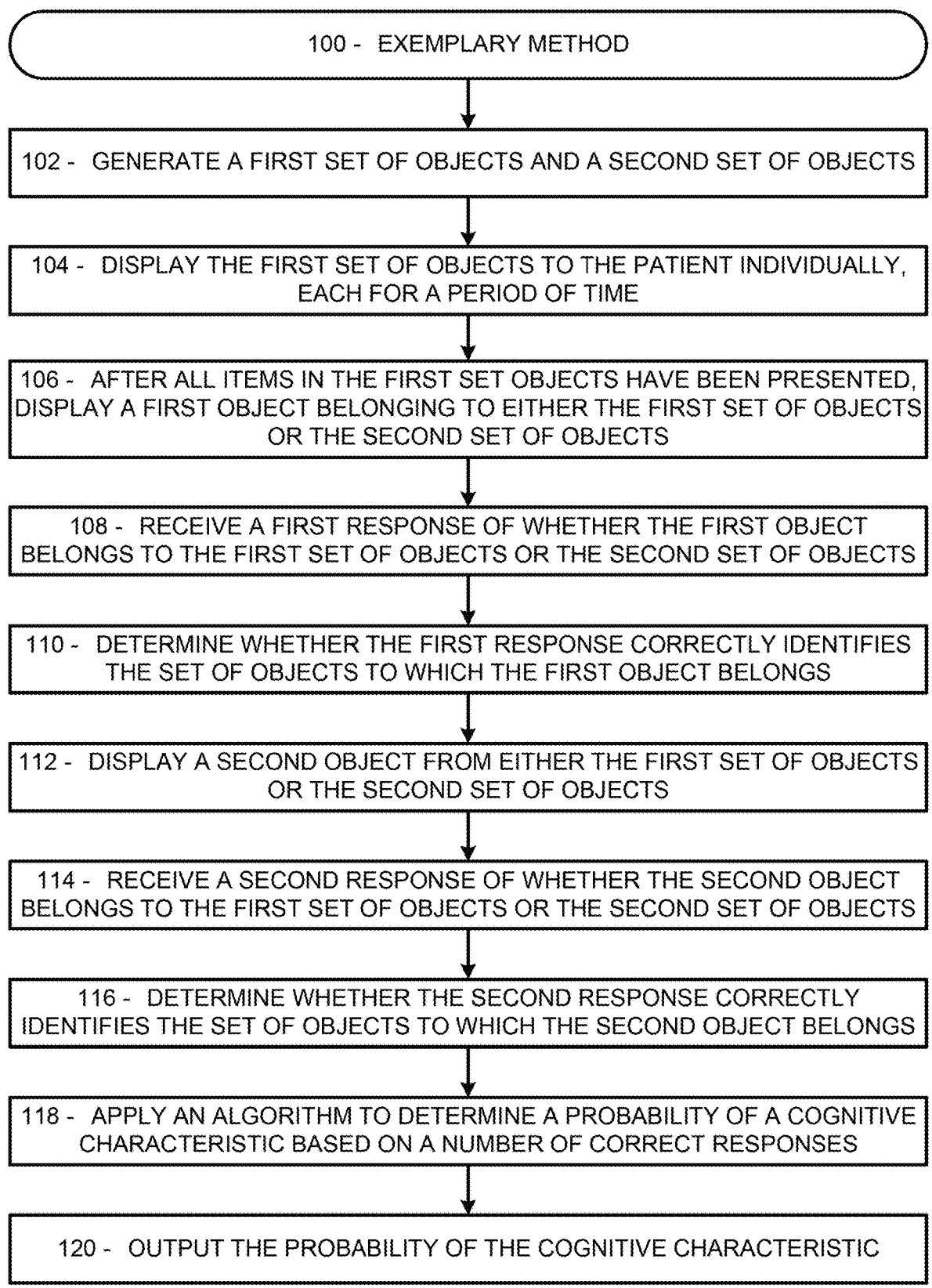
FIG. 1 illustrates a flowchart of an exemplary method for predicting a probability of cognitive impairment as contemplated by the disclosure.

The disclosure will now be described with reference to the drawing figures, in which like reference numerals refer to like parts throughout. Aspects of the disclosure advantageously provide a system and process for computerized screening and monitoring for cognitive characteristics.

Methods and systems are disclosed that predict a probability of cognitive impairment of a patient based on an automated cognitive screening tool (hereinafter "cognitive assessment"). The cognitive assessment may be completed before, during, or after a health care visit, where results may be sent to a patient's electronic medical record (EMR). The cognitive assessment may screen for cognitive impairment as well as common non-neurological factors that may contribute to cognitive concerns. For example, the cognitive assessment may include a history questionnaire and depression screen as well as verbal and nonverbal memory modules. The verbal and nonverbal memory modules may test the patient's ability to recognize images and/or words they have been asked to remember from a given set. The patient may be shown a set of images and/or words on a screen, and then asked to identify whether an image and/or a word displayed on the screen belongs to the previously displayed set. Based on the patient's responses, the cognitive assessment may determine a probability of cognitive impairment. The probability of cognitive impairment, the memory module scores, the validity indicators, the patient-provided answers to the history questionnaire, and the results of the depression screen may be output to a provider.

It is estimated that one in three adults may have cognitive concerns. Cognitive concerns may include varying levels of cognitive impairment, which may manifest in a patient as trouble remembering, learning new things, concentrating, or making decisions. Cognitive impairment may range from mild to severe. Early identification of a cognitive impairment may benefit a patient's overall health or treatment, psychosocial state, and financial situation. As a result, there is a high demand for neuropsychological services and better screening tools to identify cognitive impairment.

A cognitive assessment may be administered to a patient to screen and evaluate cognitive impairment. The cognitive assessment may be administered before, during, or after a patient sees a clinician, for example as a self-administered test completed at home prior to a clinical appointment or after the physician visit and before the patient leaves the clinic. The self-administered cognitive test can be completed in the clinical room, in a patient waiting room, at a kiosk within the clinic, on a tablet provided at the clinic, on a portal that the patient can log into using a personal electronic device that supports the assessment, or at any suitable location where patient privacy can be maintained.

The cognitive assessment may take only 10-30 minutes to complete and may be self-administered by a patient on a tablet, computer, phone, a virtual reality (VR) device, a wearable device, other implementations as described herein, or any other suitable device for the input and output of information. The cognitive assessment may be automatically scored and analyzed to yield a probability of cognitive impairment. The tablet or device may generate a report for the clinician to review, which may automatically be sent to the patient's electronic medical record (EMR) for aid in clinical decision making and/or treatment. The cognitive assessment may be utilized by any adult patient age 18 or older with any type of cognitive problem or disorder. That is, the cognitive assessment can be used by any patient regardless of their cognitive disorder, either known or unknown. The cognitive assessment may additionally include screening for and/or rating of a sleep disorder, depression, stress levels, and/or the like. The report may also indicate whether the patient speaks English as a second language.

Additionally, the self-administered design may allow for effortless screening on a population scale, due to the relative ease of administration.

A clinician may order the cognitive assessment for a specific patient, patient type, and/or a specific visit type. The patient may complete the cognitive assessment as part of an early check-in procedure or as a web-based module before the visit. Alternatively, the clinician may order the cognitive assessment after an appointment has concluded. The patient may be instructed to report to a clinician, or the clinician may direct the patient to complete the cognitive assessment as part of a web-based procedure.

After an initial assessment, the clinician may order a follow-up assessment. The follow-up assessment may be completed as part of a web-based procedure. Alternatively, the follow-up assessment may be completed during a follow-up visit with a clinician. The patient may be instructed to perform more than one follow-up assessment. The follow-up assessments may be requested or performed on a weekly basis, on a bi-weekly basis, on a monthly basis, on a bi-monthly basis (i.e., every two months) and so on. The follow-up assessments may be performed on a regular interval for a duration of up to one month, up to two months, up to three months, up to four months, up to five months, up to six months, up to a year, up to 5 years, and so on, including increments therebetween.

The cognitive assessment may include a history questionnaire (including sleep and stress related questions), a depression screen, a verbal memory module ("Word Test"), and a nonverbal memory module ("Face Test"). The history questionnaire may provide key patient demographics, medical history, and self-reported symptoms the patient may experience. The depression screen may be the Patient Health Questionnaire Depression Scale-8 item version (PHQ-8). The verbal memory module may evaluate the patient's ability to remember a set of unrelated words, while the nonverbal memory module may evaluate a patient's ability to remember faces. The memory modules may evaluate a patient's response accuracy, confidence, and response time. The clinician may receive a report on each component of the cognitive assessment; the report may include a score indicating probability of cognitive impairment, a stress rating, a quantitative stress level, average hours of sleep per night, a sleep recommendation category, a sleep score, a depression rating, a PHQ-8 score, memory scores, validity indicators, and an indication of whether the patient speaks English as a second language.

The history questionnaire may cover several subjects related to cognitive impairment, including but not limited to patient demographics, sleep habits, subjective memory, stress levels, psychiatric history, and medical history. The history questionnaire may include questions designed to provide information about a patient's mood, symptoms the patient may be experiencing, developmental history, and any relevant personal history. The results of the history questionnaire component may be output and displayed as quantitative scores (e.g., a stress level between 0-100), or qualitative descriptions (e.g., a stress rating in the minimal, moderate, or high range). Self-reported sleep habits may include average sleep duration and sleep quality. Sleep duration may be compared to the National Sleep Foundation guidelines to determine a reported sleep rating of not recommended, may be appropriate, or recommended. Sleep quality may be reported as a sleep problem rating, where the rating is none (indicating no sleep problem), mild, moderate, or severe. Patient stress levels may be displayed as a patient-reported rating of minimal, moderate, or high.

A depression screen may be included in the cognitive assessment as well, such as the standard and accepted depression screening test PHQ-8. The PHQ-8 test requires a patient to score answers on eight prompts associated with depression, where each prompt is scored between zero and three. The cognitive assessment may total the patient score and analyze to determine a depression rating for the patient. The depression rating output of the cognitive assessment may fall within five categories of minimal, mild, moderate, moderately severe, and severe. The depression rating output may also include the total raw score of the PHQ-8 screen.

The verbal memory module, or Word Test, may begin with a set of instructions and practice items. The Word Test may evaluate how quickly and accurately the patient may remember an unrelated set of words, when the set of words is interspersed with other word foils. The instructions and practice items may include an example set of words displayed on the screen, followed by a single word, where the patient is presented with a choice between identifying the single word as definitely a member of the example set, maybe a member of the example set, maybe a member of a new set, or definitely a member of the new set. After the patient has read the instructions and completed the practice items, an initial set of twenty unrelated words may be displayed on the screen individually. The initial set of twenty words (the "old" set) may be unrelated to one another. A second set of twenty unrelated words (the "new" set) may be presented as "foils" and interspersed with the "old" set of twenty words. The patient may view each word in the initial set of words for a predetermined period of time. After all words in the initial set have been presented to the patient, a set of forty words (including both "old" and "new" words) may be presented individually. The patient may be asked to identify whether the single word is a member of the old set of words, or a member of the new set of words. The patient may indicate a level of confidence in their response, choosing between response choices ranging from "definitely old" to "definitely new." After the patient indicates a response, a second word from either the old set or the new set may be displayed on the screen, and the patient may identify the second word as either a member of the old set or the new set.

This process may be repeated until all forty words from both the old set and the new set have been displayed on the screen and the patient has recorded a response for each word. The twenty words of the old set may be interspersed with the twenty words from the new set. The number of correct responses may be automatically scored by the cognitive assessment. The cognitive assessment may input the responses into an algorithm, where the number of total correct responses, response times, and the confidence levels in the response may be analyzed for cognitive impairment. The algorithm is further described below.

In addition to the Word Test, the patient may complete the nonverbal memory module ("Face Test") as a part of the cognitive assessment. The Face Test may function similarly to the Word Test component of the cognitive assessment. The Face Test may begin with a set of instructions and practice items. Practice items may include an example set of images, where the images may comprise faces, displayed on the screen. Images may be displayed in black and white. A single face may be displayed, where the patient is presented with a choice between identifying the single face as definitely a member of the example set, maybe a member of the example set, maybe a member of a new set, or definitely a member of the new set. After the patient has read the instructions and completed the practice items, an initial set of twenty faces may be displayed on the screen. The initial set of twenty faces (the "old" set) may vary in age, gender, or race. A second set of twenty faces (the "new" set) may also vary in age, gender, or race and may be presented as "foils" and interspersed with the "old" set of twenty faces. The patient may view each face in the initial set of faces for a predetermined period of time. After all faces in the initial set have been presented to the patient, a set of forty faces (both "old" and "new" faces) may be presented individually.

The patient may be asked to identify whether the single face is a member of the old set of faces, or a member of the new set of faces. The patient may indicate their level of confidence in their response, choosing between response choices ranging from "definitely old" to "definitely new." After the patient indicates a response, a second face from either the old set or the new set may be displayed on the screen, and the patient may identify the second face as either a member of the old set or the new set.

This process may be repeated until all forty faces from both the old set and the new set have been displayed on the screen and the patient has recorded a response for each face. The twenty faces of the old set may be interspersed with the twenty faces from the new set. The number of correct responses may be automatically scored by the cognitive assessment. The responses may be input into an algorithm, where the number of total correct responses, response times, and the confidence levels in the response may be analyzed for cognitive impairment. The algorithm is further described below.

Once the patient has completed the questionnaire, depression screen, and both memory modules, responses to each component may be input into a predictive algorithm for analysis. The predictive algorithm may output a probability of cognitive impairment present, memory scores, validity indicators, a depression rating, a sleep rating (including both duration and quality), a stress rating, and a cautionary flag for English-Second-Language examinee. The algorithm may be a heuristic algorithm such as a weighted sum, where results are combined into one scalar, objective function. The function may comprise variables having different weights, with variables identified as more important to report corresponding to a higher weight. For example, the score from the Word Test component of the cognitive assessment may have a higher weight than the responses to the history questionnaire component. Weights may be predetermined by a clinician, statistically derived from a validation set, or provided in any other suitable manner.

Alternatively, the algorithm may be a machine learning algorithm or artificial intelligence algorithm trained by processing a plurality of training responses to identify the presence of a cognitive impairment. Any other suitable algorithm may be used in conjunction with the cognitive assessment.

The algorithm may have a series of validated thresholds, to which a resulting score may be compared. Thresholds may be determined by the clinician, through statistical analysis, or any other suitable method.

A validation set may be used to test the predictive accuracy of the cognitive assessment. For example, a validation sample may include administering the cognitive assessment to a group of adults over the age of 18, comprising both males and females from a variety of demographics, with varying levels of education. Results of the cognitive assessment may be validated against a reliable neuropsychological assessment. The algorithm has been shown to have a predictive accuracy that outperforms the leading screening test, with predicted probabilities closely matching observed proportions of impairment.

The probability of cognitive impairment may be based on the patient responses to all three components and may be presented to the clinician as a number on the scale of 0-100 or as a percentage. The output may include validated thresholds based on how well (e.g., how accurately and how confidently) the patient correctly identified the words and images as new or old. The cut points may be input by a clinician or may be based on statistically relevant findings.

Alternatively, the probability of cognitive impairment may be displayed to a clinician as the probability that the patient would demonstrate impairment on a comprehensive cognitive assessment.

Alternatively, the probability of cognitive impairment may be displayed as a nomogram, or as a comparison (i.e., "in 100 patients just like you, 93 would have a cognitive problem.").

A positive or negative prediction value may accompany the probability output to reassure a clinician that a likelihood of cognitive impairment is accurate.

The method may include an additional algorithm that uses aspects of memory module performance (i.e., response patterns, response times) to identify patterns that may indicate invalid test performance or absence of optimal effort during test performance. Output may include a flag to indicate invalid performance.

FIG. 1 illustrates a flowchart of an exemplary method for predicting a probability of cognitive impairment as contemplated by the disclosure.

Figure 3:
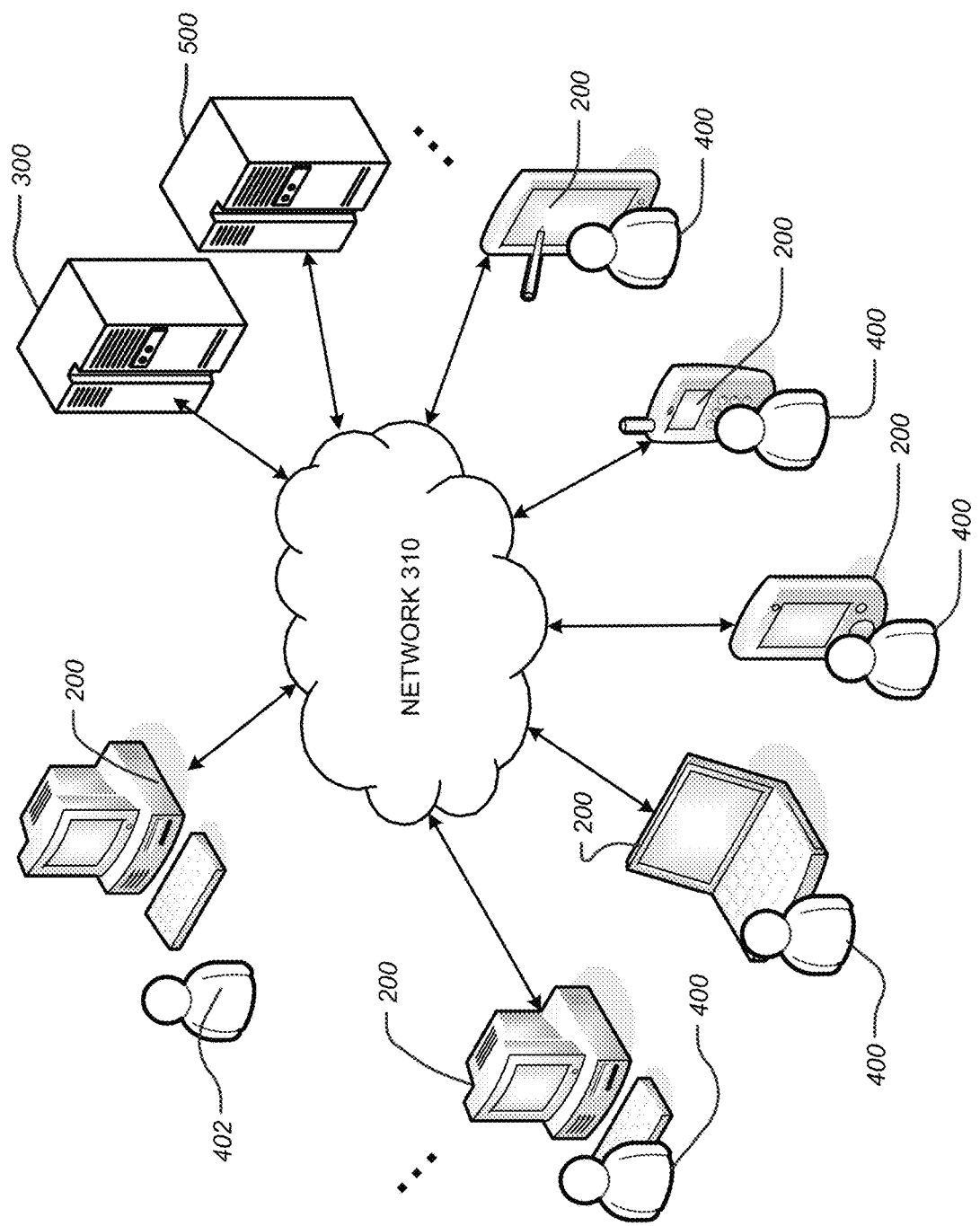
FIG. 3 illustrates exemplary configurations and implementations of the computing device and/or the system according to aspects of the disclosure.

In particular, FIG. 1 illustrates a flowchart of an exemplary method for predicting a probability of cognitive impairment 100. For example, the exemplary method for predicting a probability of cognitive impairment 100 may be implemented by a computing device 200, a system 300, and/or the like as illustrated in FIG. 3. In aspects, the exemplary method for predicting a probability of cognitive impairment 100 may be implemented in part by the computing device 200, the system 300, and/or the like. In aspects, the computing device 200 may be implemented as a portal computer, a mobile phone, a tablet, a virtual reality (VR) device, a wearable device, other implementations as described herein, and/or the like. In aspects, the computing device 200 may be implemented by a processor, a server, and/or the like. Moreover, the exemplary method for predicting a probability of cognitive impairment 100 may be performed automatically, in response to a request by a clinician 402, and/or the like. In aspects, the exemplary method for predicting a probability of cognitive impairment 100 may be implemented as an app or application executed by the computing device 200. In aspects, the exemplary method for predicting a probability of cognitive impairment 100 may be implemented as a web-based application executed by the computing device 200 and/or the system 300.

According to one embodiment, the exemplary method for predicting a probability of cognitive impairment 100 may include one or more of the following steps. In particular, it should be noted that the exemplary method for predicting a probability of cognitive impairment 100 is merely exemplary and may be modified consistent with the various aspects disclosed herein. It should be noted that the exemplary method for predicting a probability of cognitive impairment 100 may be performed in a different order consistent with the aspects described above. Moreover, the exemplary method for predicting a probability of cognitive impairment 100 may be modified to have more or fewer process steps consistent with the various aspects disclosed herein.

In step 102, the exemplary method for predicting a probability of cognitive impairment 100 may include generating a first set of objects and a second set of objects. The objects in both the first set and the second set may be generated randomly from an object bank. Alternatively, the objects may be predetermined by the clinician 402. Each set of objects may be a discrete set, where no object that is a member of the first set may be a member of the second set.

The objects may be words, generated by a word bank and presented as a word list. The objects may also be images, such as black and white or color images of faces generated by the system from an image bank. Alternatively, the images may be predetermined by the clinician 402 and input into the computing device 200, the system 300, and/or the like.

In step 104, the exemplary method for predicting a probability of cognitive impairment 100 may include displaying the first set of objects to the patient 400 on a display of the computing device 200, where the set of objects are displayed individually, each for a period of time. The period of time may be a standard length of time for the cognitive assessment, the clinician 402 may select a predetermined amount of time, and/or the like. The computing device 200 and/or the system 300 may automatically advance to a next step or advance in response to a request from either the clinician 402 or the patient 400.

In step 106, the exemplary method for predicting a probability of cognitive impairment 100 may include, after each item in the first set of objects has been presented, displaying on the computing device 200 a first object belonging to either the first set of objects or to the second set of objects. The first object may be prominently displayed on a screen of the computing device 200, with a set of possible responses for the patient 400 to select displayed on the computing device 200 below the object. The first object may be displayed on the computing device 200 for a predetermined time, or it may be displayed on the computing device 200 until the patient 400 selects a first response of the set of possible responses.

In step 108, the exemplary method for predicting a probability of cognitive impairment 100 may include receiving a first response in the computing device 200 from the patient 400 indicating whether the first object belongs to the first set of objects or to the second set of objects. The responses may include an indication of which set the object belongs to, and a level of confidence the patient 400 has in their response (e.g., definitely a member of the first set, may be a member of the first set, definitely a member of the second set, may be a member of the second set, and/or the like).

In step 110, the exemplary method for predicting a probability of cognitive impairment 100 may include determining whether the first response correctly identifies the set of objects to which the first object belongs. The computing device 200 and/or the system 300 may compare the response to an answer key. The level of confidence the patient 400 has indicated, the time to respond, and/or the like may be logged in the system 300 and/or the computing device 200 for further analysis.

In step 112, the exemplary method for predicting a probability of cognitive impairment 100 may include displaying on the computing device 200 a second object from either the first set of objects or the second set of objects. The second object may belong to the same set as the first object or may belong to the other set of objects. The order in which objects are displayed on the computing device 200 may be random or may be predetermined by the system 300 and/or the computing device 200.

In step 114, the exemplary method for predicting a probability of cognitive impairment 100 may include receiving a second response in the computing device 200 from the patient 400 of whether the second object belongs to the first set of objects or the second set of objects. The response may include the indication of which set the object belongs to, as well as the level of confidence the patient 400 has in their answer.

In step 116, the exemplary method for predicting a probability of cognitive impairment 100 may include determining whether the second response correctly identifies the set of objects to which the second object belongs. The system 300 and/or the computing device 200 may compare the second response to an answer key, and may log the first and second responses to create an overall total of correct responses. The steps 108-116 may be iteratively repeated by the computing device 200 and/or the system 300 until each object from the first set of objects and each object from the second set of objects has been displayed on the computing device 200, and a response of which set the object belongs to has been received. The order in which the objects are displayed by the computing device 200 may be random, and each object may be displayed only once. Alternatively, the order in which the objects are displayed by the computing device 200 may be predetermined by the clinician 402. The order may be the same for each application of the exemplary method for predicting a probability of cognitive impairment 100 by the computing device 200 and/or the system 300.

In step 118, the exemplary method for predicting a probability of cognitive impairment 100 may include applying an algorithm to determine a probability of a cognitive characteristic based on a number of correct responses. The algorithm may be implemented by the computing device 200 and/or the system 300 and additionally take, as input, a confidence level associated with each answer (i.e., whether the patient 400 has answered definitely a member of one set, or maybe a member of one set). The algorithm may also include an input of response time, as well as answers to the patient questionnaire and depression screening. The algorithm may be a heuristic algorithm, a machine learning algorithm, artificial or any other suitable algorithm. The algorithm may be trained or may be a weighted sum predetermined by the computing device 200 and/or the system 300 based on a statistically relevant model.

In step 120, the exemplary method for predicting a probability of cognitive impairment 100 may include outputting a probability of the cognitive characteristic. The probability may be output as a part of a report, which may include other information about the patient 400. The report may include information about the patient's sleep, mood, stress levels, and whether the patient 400 speaks English as a second language. The report may also include memory test scores or validity indicators, which may report on aspects of the memory module performance (i.e., response patterns, response times, etc.) and identified patterns indicating invalid test performance or absence of optimal effort during test performance. The computing device 200 and/or the system 300 may generate the report and display the report, print the report, and/or the like. The computing device 200 and/or the system 300 may automatically send the report to the patient's EMR for review by the clinician 402. In particular, the computing device 200 and/or the system 300 may be connected to an electronic medical records (EMR) system 500.

Figure 2A:
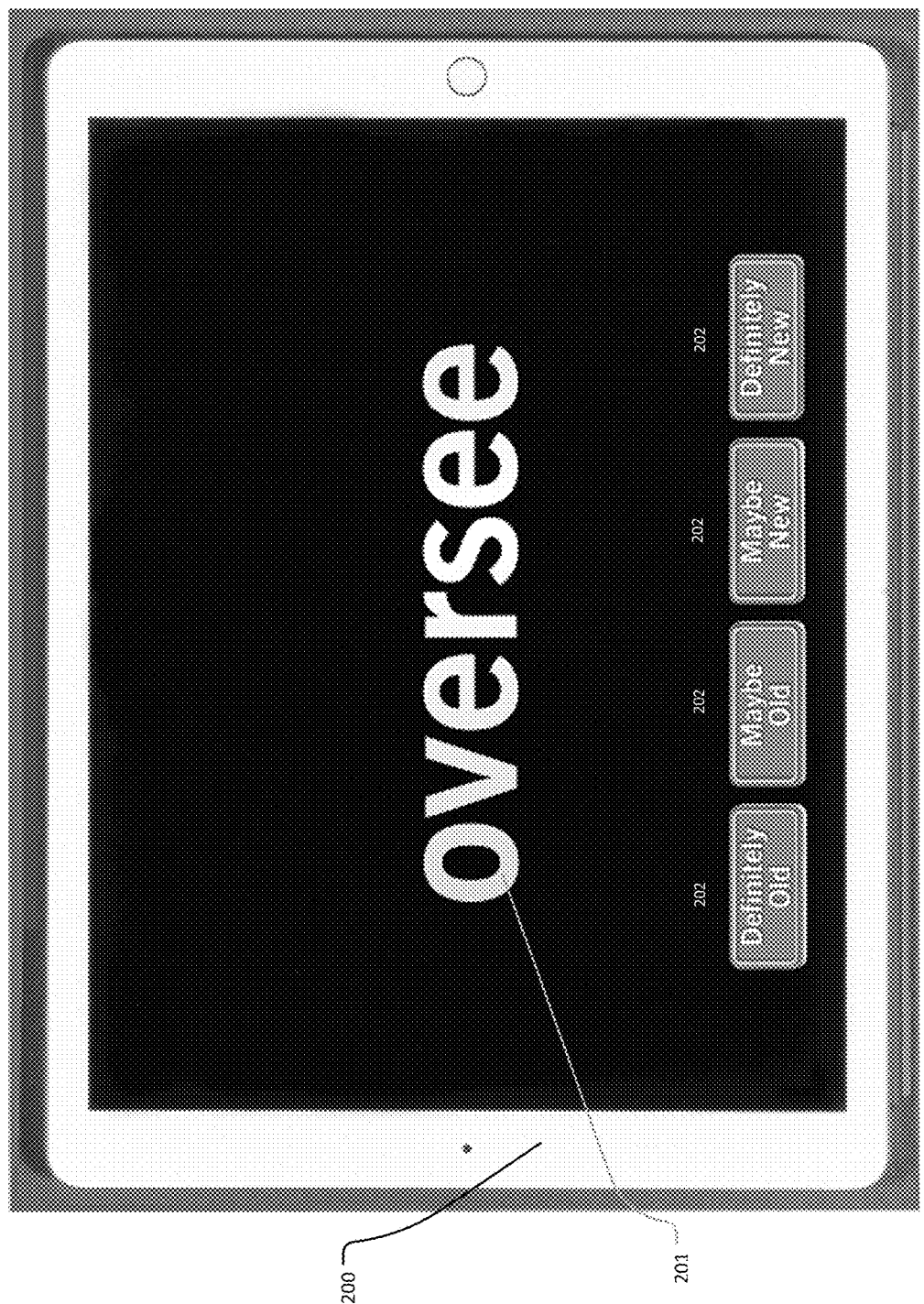
FIG. 2A and FIG. 2B illustrate an exemplary display of a computing device displaying an object with a set of responses according to aspects of the disclosure.
Figure 2B:
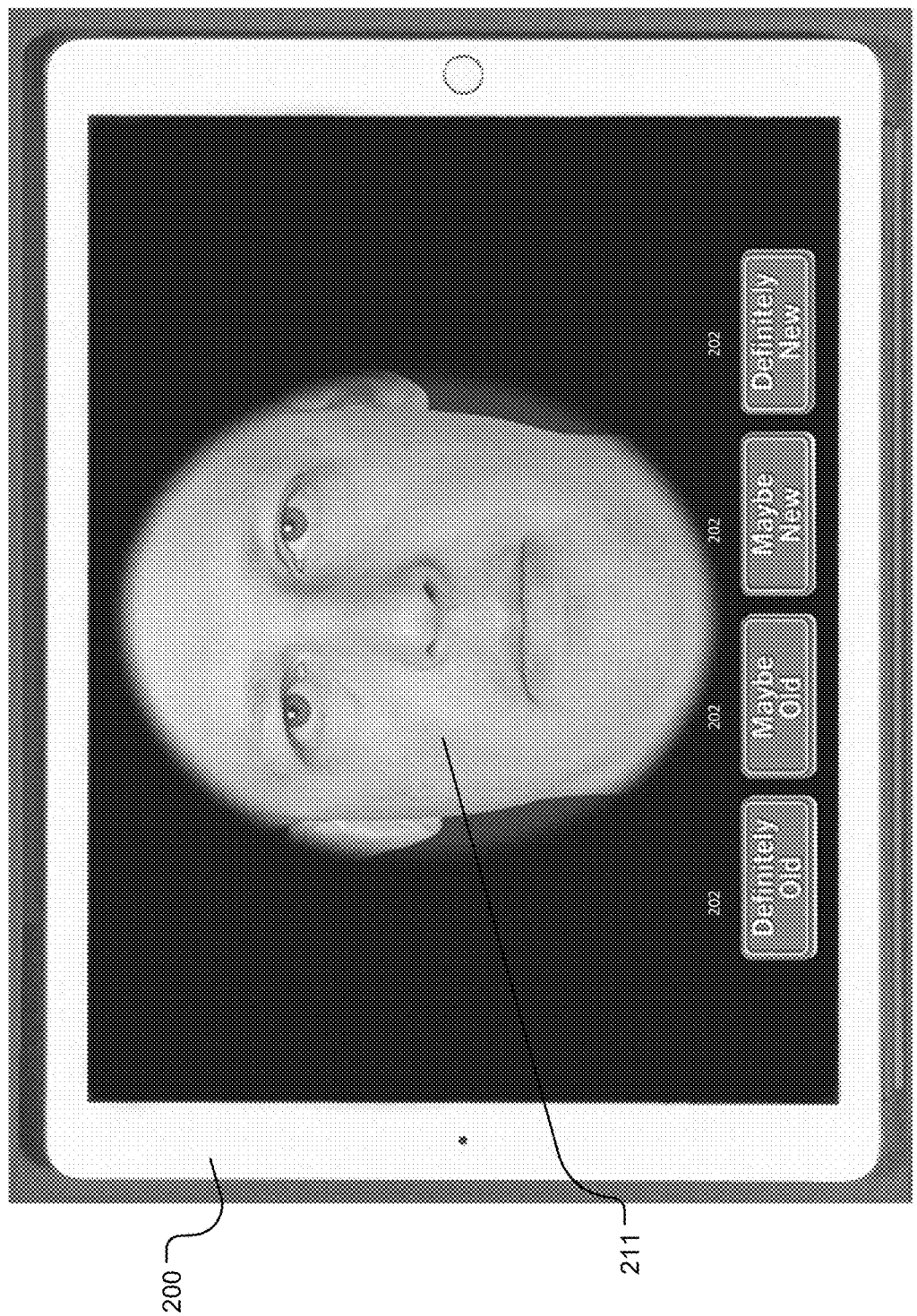

FIG. 2A and FIG. 2B illustrate an exemplary display of a computing device displaying an object with a set of responses according to aspects of the disclosure.

In particular, FIG. 2 illustrates an exemplary display of the computing device 200 displaying an object with a set of responses. The computing device 200 may display an object, such as word 201. The computing device 200 may be a portal computer, a mobile phone, a tablet, a virtual reality (VR) device, a wearable device, other implementations as described herein, any other suitable device, and/or the like. The word 201 may be a member of either a first word list or a second word list, where both lists have been generated by the computing device 200 from a word bank. The first and second word lists may comprise the same words in the same order for each application of the method. The first word list may be referred to as the "old" set, such that the patient 400 may select a response 202 indicating that the displayed word is a member of the old list that was previously displayed by the computing device 200. The "new" set is not displayed to the patient 400 as a whole. The members of the new set may be randomly interspersed with the old set or may be displayed in a predetermined order selected by the clinician 402. The computing device 200 may display a number of responses 202, which may include "definitely old", "maybe old", "maybe new", and "definitely new." The patient 400 may choose a response based on how confident they are in their answer of old or new set. In aspects, the responses 202 implemented by the computing device 200 may be virtual input buttons, actual input buttons, radio input buttons, voice recognition inputs, keyboard inputs, mouse inputs, and/or the like.

Likewise, the computing device 200 may display an image 211, which may be a black and white image of a face. The image 211 may be generated by the computing device 200 from an image bank, or may be predetermined by the clinician 402. The computing device 200 and/or the system 300 may generate a first ("old") set of images and a second ("new") set of images. The old set may be displayed to the patient 400 by the computing device 200 prior to an individual image 211 being displayed on the computing device 200. The patient 400 may be presented with the responses 202 along with the image 211, and the patient 400 may choose between the options of definitely old, maybe old, maybe new, and definitely new in regard to which set the image belongs.

FIG. 3 illustrates exemplary configurations and implementations of the computing device and/or the system according to aspects of the disclosure.

In particular, FIG. 3 illustrates exemplary configurations and implementations of the computing device 200 and/or the system 300. In aspects, the computing device 200 and/or the system 300 may be implemented by a smartphone, a server computer, a workstation, an access point, a router, a gateway, a tablet computer, a laptop computer, a notebook computer, a desktop computer, a personal computer, a virtual reality (VR) device, a wearable device, a network appliance, a PDA, an e-reader, a user equipment (UE), a mobile station, a fixed mobile subscriber unit, a mobile subscriber unit, a pager, a wireless sensor, a consumer electronics device, other computing device, and/or the like and may be utilized to execute any aspects of the methods and apparatus described herein, such as to implement the exemplary method for predicting a probability of cognitive impairment 100 of FIG. 1.

In aspects, the patient 400 may interact with the computing device 200 as illustrated in FIG. 3. Moreover, the computing device 200 may interact with the system 300 over a communications network 310. Additionally, the clinician 402 may interact with their own implementation of the computing device 200 as illustrated in FIG. 3. Moreover, the computing device 200 implemented by the clinician 402 may interact with the system 300 over the communications network 310.

In aspects, the exemplary method for predicting a probability of cognitive impairment 100 in conjunction with the computing device 200 and/or the system 300 may be configured for cognitive assessments for use as screening tools for cognitive impairment. In aspects, the exemplary method for predicting a probability of cognitive impairment 100 in conjunction with the computing device 200 and/or the system 300 may be configured for patient-administered cognitive assessment that integrates into electronic medical records of the electronic medical record (EMR) system 500 and provides clinicians with patient-provided cognitive data for aiding in clinical decision-making. In aspects, the exemplary method for predicting a probability of cognitive impairment 100 may be configured such that it may be self-administered by the patient 400 on the computing device 200.

In aspects, the exemplary method for predicting a probability of cognitive impairment 100 may be configured such that the clinician 402 may administer and give the test from any and all computing device platforms.

In aspects, the computing device 200 may be implemented as VR devices both standalone and tethered. In aspects, the exemplary method for predicting a probability of cognitive impairment 100 may be administered via a VR headset implementation of the computing device 200.

In aspects, the exemplary method for predicting a probability of cognitive impairment 100 in conjunction with the computing device 200 and/or the system 300 may be configured to collect longitudinal data where testing and retesting is performed.

In aspects, the exemplary method for predicting a probability of cognitive impairment 100 in conjunction with the computing device 200 and/or the system 300 may be configured for fully automated testing, scoring, and reporting of cognitive screening. In aspects, the exemplary method for predicting a probability of cognitive impairment 100 in conjunction with the computing device 200 and/or the system 300 may be configured as a fully self-administered screening tool that can be completed in public or private spaces (i.e., clinic rooms, waiting rooms, intake kiosks). In aspects, the exemplary method for predicting a probability of cognitive impairment 100 in conjunction with the computing device 200 and/or the system 300 may be configured to be instantaneously scored, and results are automatically documented in the patient's EMR. In aspects, the exemplary method for predicting a probability of cognitive impairment 100 in conjunction with the computing device 200 and/or the system 300 may be more scalable than existing paper-and-pencil approaches or supervised computerized tools.

In aspects, the exemplary method for predicting a probability of cognitive impairment 100 in conjunction with the computing device 200 and/or the system 300 may be configured with a psychometric design. In aspects, the exemplary method for predicting a probability of cognitive impairment 100 in conjunction with the computing device 200 and/or the system 300 may be configured with a design that exploits decades of cognitive neuroscience research. In aspects, the exemplary method for predicting a probability of cognitive impairment 100 in conjunction with the computing device 200 and/or the system 300 may be configured to avoid the ceiling effects that reduce sensitivity in other screening tools.

In aspects, the exemplary method for predicting a probability of cognitive impairment 100 in conjunction with the computing device 200 and/or the system 300 may be configured for concurrent screening for treatable contributing factors. In aspects, the exemplary method for predicting a probability of cognitive impairment 100 in conjunction with the computing device 200 and/or the system 300 may be configured to identify problematic depression, sleep, and stress that providers can act on to optimize cognitive function.

In aspects, the exemplary method for predicting a probability of cognitive impairment 100 in conjunction with the computing device 200 and/or the system 300 may be configured for disease agnostic screening. In aspects, the exemplary method for predicting a probability of cognitive impairment 100 in conjunction with the computing device 200 and/or the system 300 may be configured as a cognitive risk calculator configured to apply to a wide range of disorders, avoiding a myopic focus on a specific phenotype at the expense of missing others.

In aspects, the exemplary method for predicting a probability of cognitive impairment 100 in conjunction with the computing device 200 and/or the system 300 may be configured for integration with the electronic medical records (EMR) system 500. In aspects, the exemplary method for predicting a probability of cognitive impairment 100 in conjunction with the computing device 200 and/or the system 300 may be configured to facilitate ordering and provide real-time results and treatment recommendations to the clinician 402.

In aspects, the exemplary method for predicting a probability of cognitive impairment 100 in conjunction with the computing device 200 and/or the system 300 may be configured to be integrated with risk calculators. In aspects, the exemplary method for predicting a probability of cognitive impairment 100 in conjunction with the computing device 200 and/or the system 300 may incorporate direct links to other clinics or medical facilities to facilitate patient-initiated referrals. For example, sleep evaluation and treatment.

In aspects, the exemplary method for predicting a probability of cognitive impairment 100 in conjunction with the computing device 200 and/or the system 300 may be configured to predict a probability of cognitive impairment of the patient 400 based on implementation of an automated cognitive screening tool. The cognitive assessment may be completed before, during, or after a health care visit, where results may be sent to the electronic medical records (EMR) system 500. The cognitive assessment may screen the patient 400 for cognitive impairment as well as common non-neurological factors that may contribute to cognitive concerns.

In aspects, the exemplary method for predicting a probability of cognitive impairment 100 in conjunction with the computing device 200 and/or the system 300 may be configured to implement the cognitive assessment, which may include a history questionnaire and depression screen as well as verbal and nonverbal memory modules. The verbal and nonverbal memory modules may test the patient's ability to recognize images and/or words they have been asked to remember from a given set. In aspects, the exemplary method for predicting a probability of cognitive impairment 100 in conjunction with the computing device 200 and/or the system 300 may be configured to show the patient 400 a set of images and/or words on a screen, and then asked to identify whether an image and/or a word displayed on the screen belongs to the previously displayed set. Based on the patient's responses, the cognitive assessment may determine a probability of cognitive impairment. The probability of cognitive impairment, the memory module scores, the validity indicators, the patient-provided answers to the history questionnaire, and the results of the depression screen may be output to the clinician 402 and/or the electronic medical records (EMR) system 500.

In aspects, the exemplary method for predicting a probability of cognitive impairment 100 in conjunction with the computing device 200 and/or the system 300 may be configured to be administered to the patient 400 to screen and evaluate cognitive impairment. The cognitive assessment may be administered before, during, or after the patient 400 sees the clinician 402, for example as a self-administered test completed at home prior to a clinical appointment or after the physician visit and before the patient leaves the clinic. In aspects, the exemplary method for predicting a probability of cognitive impairment 100 in conjunction with the computing device 200 and/or the system 300 may be configured to be a self-administered cognitive test that can be completed in the clinical room, in a patient waiting room, at a kiosk within the clinic, on a tablet provided at the clinic, on a portal that the patient can log into using a personal electronic device that supports the assessment, or at any suitable location where patient privacy can be maintained.

In aspects, the exemplary method for predicting a probability of cognitive impairment 100 in conjunction with the computing device 200 and/or the system 300 may be configured to be automatically scored and analyzed to yield a probability of cognitive impairment of the patient 400. The computing device 200 and/or the system 300 may generate a report for the clinician 402 to review, which may automatically be sent to the electronic medical record (EMR) system 500 for aid in clinical decision making and/or treatment. In aspects, the exemplary method for predicting a probability of cognitive impairment 100 in conjunction with the computing device 200 and/or the system 300 may be configured such that the cognitive assessment may additionally include screening for and/or rating of a sleep disorder, depression, stress levels, and/or the like. The report may also indicate whether the patient speaks English as a second language.

In aspects, the exemplary method for predicting a probability of cognitive impairment 100 in conjunction with the computing device 200 and/or the system 300 may be configured to be self-administered, which may allow for effortless screening on a population scale, due to the relative ease of administration.

In aspects, the exemplary method for predicting a probability of cognitive impairment 100 in conjunction with the computing device 200 and/or the system 300 may be configured such that the clinician 402 may order the cognitive assessment for a specific patient, patient type, and/or a specific visit type. The patient 400 may complete the cognitive assessment as part of an early check-in procedure or as a web-based module before the visit. Alternatively, the clinician 402 may order the cognitive assessment after an appointment has concluded.

In aspects, the exemplary method for predicting a probability of cognitive impairment 100 in conjunction with the computing device 200 and/or the system 300 may be configured, after an initial assessment, such that the clinician 402 may order a follow-up assessment. The follow-up assessment may be completed as part of a web-based procedure. Alternatively, the follow-up assessment may be completed during a follow-up visit with the clinician 402. The patient 400 may be instructed to perform more than one follow-up assessment. The follow-up assessments may be requested or performed on a weekly basis, on a bi-weekly basis, on a monthly basis, on a bi-monthly basis (i.e., every two months) and so on by interaction with the computing device 200 and/or the system 300. The follow-up assessments may be performed on a regular interval for a duration of up to one month, up to two months, up to three months, up to four months, up to five months, up to six months, up to a year, up to 5 years, and so on, including increments therebetween.

In aspects, the exemplary method for predicting a probability of cognitive impairment 100 in conjunction with the computing device 200 and/or the system 300 may be configured to implement a cognitive assessment that may include a history questionnaire (including sleep and stress related questions), a depression screen, a verbal memory module ("Word Test"), and a nonverbal memory module ("Face Test"). The history questionnaire may provide key patient demographics, medical history, and self-reported symptoms the patient may experience. The depression screen may be the Patient Health Questionnaire Depression Scale-8 item version (PHQ-8). The verbal memory module may evaluate the patient's ability to remember a set of unrelated words, while the nonverbal memory module may evaluate a patient's ability to remember faces. The memory modules may evaluate a patient's response accuracy, confidence, and response time. The clinician 402 may receive a report on each component of the cognitive assessment; the report may include a score indicating probability of cognitive impairment, a stress rating, a quantitative stress level, average hours of sleep per night, a sleep recommendation category, a sleep score, a depression rating, a PHQ-8 score, memory scores, validity indicators, and an indication of whether the patient speaks English as a second language.

The history questionnaire may cover several subjects related to cognitive impairment, including but not limited to patient demographics, sleep habits, subjective memory, stress levels, psychiatric history, and medical history. The history questionnaire may include questions designed to provide information about a patient's mood, symptoms the patient may be experiencing, developmental history, and any relevant personal history. The results of the history questionnaire component may be output and displayed as quantitative scores (e.g., a stress level between 0-100), or qualitative descriptions (e.g., a stress rating in the minimal, moderate, or high range) by the computing device 200 and/or the system 300. Self-reported sleep habits may include average sleep duration and sleep quality. Sleep duration may be compared to the National Sleep Foundation guidelines to determine a reported sleep rating of not recommended, may be appropriate, or recommended. Sleep quality may be reported as a sleep problem rating, where the rating is none (indicating no sleep problem), mild, moderate, or severe. Patient stress levels may be displayed as a patient-reported rating of minimal, moderate, or high.

In aspects, the exemplary method for predicting a probability of cognitive impairment 100 in conjunction with the computing device 200 and/or the system 300 may be configured to implement a depression screen that may be included in the cognitive assessment as well, such as the standard and accepted depression screening test PHQ-8. The PHQ-8 test requires a patient to score answers on eight prompts associated with depression, where each prompt is scored between zero and three. The cognitive assessment may total the patient score and analyze to determine a depression rating for the patient 400. The depression rating output of the cognitive assessment may fall within five categories of minimal, mild, moderate, moderately severe, and severe. The depression rating output may also include the total raw score of the PHQ-8 screen.

In aspects, the exemplary method for predicting a probability of cognitive impairment 100 in conjunction with the computing device 200 and/or the system 300 may be configured such that once the patient 400 has completed the questionnaire, depression screen, and both memory modules, responses to each component may be input into a predictive algorithm for analysis by the computing device 200 and/or the system 300. The predictive algorithm may output a probability of cognitive impairment present, memory scores, validity indicators, a depression rating, a sleep rating (including both duration and quality), a stress rating, and a cautionary flag for English-Second-Language examinee. The algorithm implemented by the computing device 200 and/or the system 300 may be a heuristic algorithm such as a weighted sum, where results are combined into one scalar, objective function. The function may comprise variables having different weights, with variables identified as more important to report corresponding to a higher weight. For example, the score from the Word Test component of the cognitive assessment may have a higher weight than the responses to the history questionnaire component. Weights may be predetermined by a clinician, statistically derived from a validation set, or provided in any other suitable manner.

Alternatively, the algorithm implemented by the computing device 200 and/or the system 300 may be a machine learning algorithm or artificial intelligence algorithm trained by processing a plurality of training responses to identify the presence of a cognitive impairment. Any other suitable algorithm may be used in conjunction with the cognitive assessment.

The algorithm implemented by the computing device 200 and/or the system 300 may have a series of validated thresholds, to which a resulting score may be compared. Thresholds may be determined by the clinician 402, through statistical analysis, and/or any other suitable method.

In aspects, the exemplary method for predicting a probability of cognitive impairment 100 in conjunction with the computing device 200 and/or the system 300 may be configured to utilize a validation set that may be used to test the predictive accuracy of the cognitive assessment. For example, a validation sample may include administering the cognitive assessment to a group of adults over the age of 18, comprising both males and females from a variety of demographics, with varying levels of education. Results of the cognitive assessment implemented by the computing device 200 and/or the system 300 may be validated against a reliable neuropsychological assessment. The algorithm implemented by the computing device 200 and/or the system 300 has been shown to have a predictive accuracy that outperforms the leading screening test, with predicted probabilities closely matching observed proportions of impairment.

In aspects, the exemplary method for predicting a probability of cognitive impairment 100 in conjunction with the computing device 200 and/or the system 300 may be configured such that a resulting probability of cognitive impairment may be based on the patient responses to all three components and may be presented to the clinician 402 as a number on the scale of 0-100 or as a percentage. The output may include validated thresholds based on how well (e.g., how accurately and how confidently) the patient 400 correctly identified the words and images as new or old. The cut points may be input by the clinician 402 or may be based on statistically relevant findings.

In aspects, the exemplary method for predicting a probability of cognitive impairment 100 in conjunction with the computing device 200 and/or the system 300 may be configured such that the probability of cognitive impairment may be displayed to the clinician 402 as the probability that the patient 400 would demonstrate impairment on a comprehensive cognitive assessment.

In aspects, the exemplary method for predicting a probability of cognitive impairment 100 in conjunction with the computing device 200 and/or the system 300 may be configured such that the probability of cognitive impairment may be displayed by the computing device 200 and/or the system 300 as a nomogram, or as a comparison (i.e., "in 100 patients just like you, 93 would have a cognitive problem."). A positive or negative prediction value may accompany the probability output to reassure the clinician 402 that a likelihood of cognitive impairment is accurate.

In aspects, the exemplary method for predicting a probability of cognitive impairment 100 in conjunction with the computing device 200 and/or the system 300 may be configured to include an additional algorithm that uses aspects of memory module performance (i.e., response patterns, response times) to identify patterns that may indicate invalid test performance or absence of optimal effort during test performance. Output may include a flag to indicate invalid performance.

Figure 4:
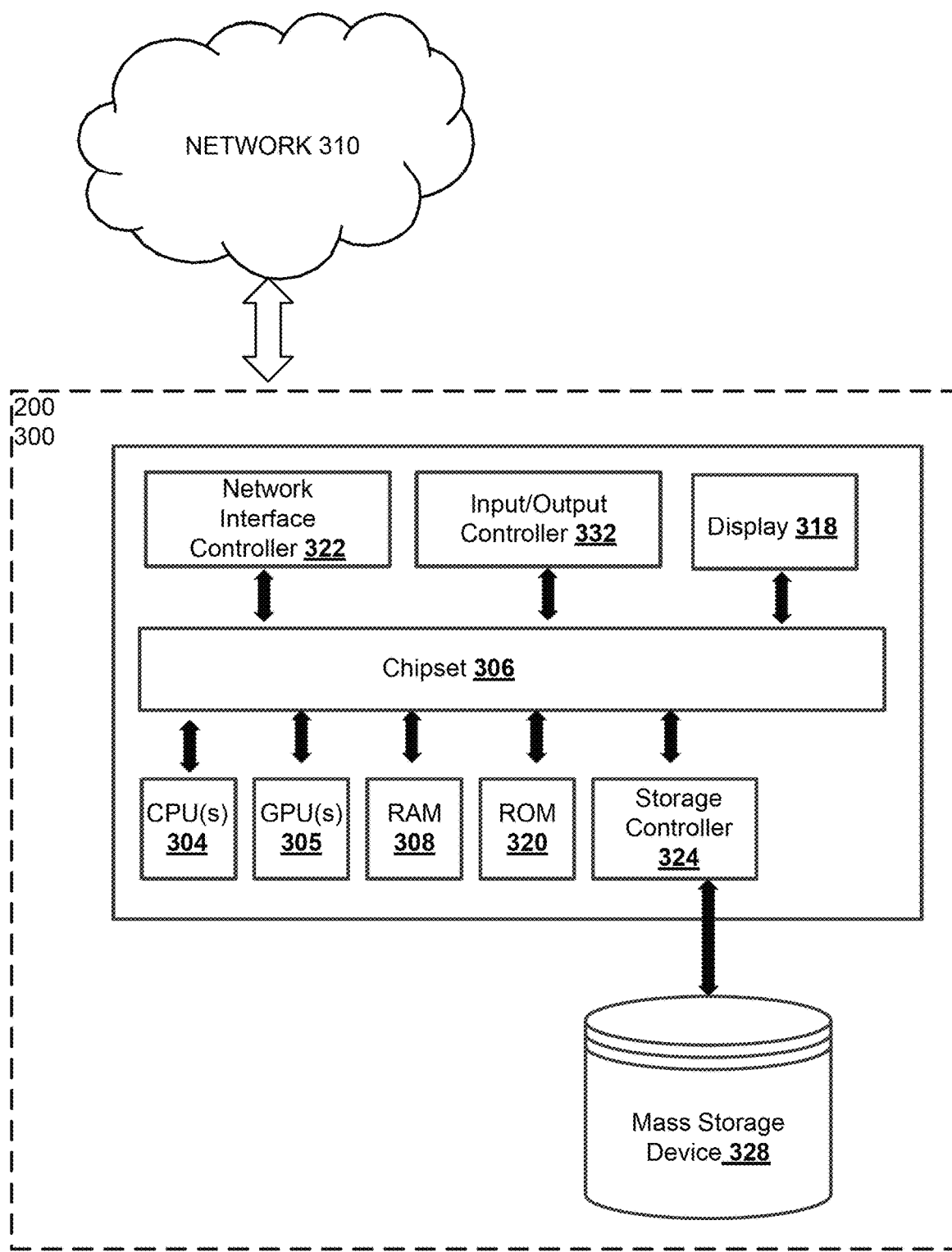
FIG. 4 illustrates further exemplary details of the computing device and/or the system according to aspects of the disclosure.

FIG. 4 illustrates further exemplary details of the computing device and/or the system according to aspects of the disclosure.

The computing device 200 and/or the system 300 may include a display 318. In an exemplary aspect, a touchscreen may be implemented in the display 318 and may detect a presence and location of a touch of the patient 400 within the display area. For example, touching the display 318 of the computing device 200 with a finger or hand. The touchscreen may also sense other passive objects, such as a stylus. The touchscreen may further include a touch screen controller.

In operation, the display 318 may show the responses 202. For example, the patient 400 may touch the display 318, particularly the touchscreen, to interact with the responses 202. That is, touching the responses 202 may be an input in response to the exemplary method for predicting a probability of cognitive impairment 100. The display 318 may include a plurality of the responses 202 for the patient 400 to interact with. Moreover, the display 318 may include a plurality of screens. The display 318 showing one screen at a time.

The touchscreen may be implemented as a resistive touchscreen, a surface acoustic wave touch screen, a capacitive touch screen, a surface capacitance touchscreen, projected capacitive touch screen, self-capacitance sensors, infrared sensors, dispersive signal technology, acoustic pulse recognition, and/or the like.

The computing device 200 and/or the system 300 may include a baseboard, or "motherboard," which is a printed circuit board to which a multitude of components or devices may be connected by way of a system bus or other electrical communication paths. One or more central processing units, processors, and/or the like hereinafter CPU(s) 304, may operate in conjunction with a chipset 306. The CPU(s) 304 may be standard programmable processors that perform arithmetic and logical operations necessary for the operation of 200 and/or the system 300.

The CPU(s) 304 may perform the necessary operations by transitioning from one discrete physical state to the next through the manipulation of switching elements that differentiate between and change these states. Switching elements may generally include electronic circuits that maintain one of two binary states, such as flip-flops, and electronic circuits that provide an output state based on the logical combination of the states of one or more other switching elements, such as logic gates. These basic switching elements may be combined to create more complex logic circuits including registers, adders-subtractors, arithmetic logic units, floating-point units, and the like.

The CPU(s) 304 may be augmented with or replaced by other processing units, such as GPU(s) 305. The GPU(s) 305 may comprise processing units specialized for but not necessarily limited to highly parallel computations, such as graphics and other visualization-related processing.

The chipset 306 may provide an interface between the CPU(s) 304 and the remainder of the components and devices on the baseboard. The chipset 306 may provide an interface to a random access memory (RAM) 308 used as the main memory in 200 and/or the system 300. The chipset 306 may provide an interface to a computer-readable storage medium, such as a read-only memory (ROM) 320 or non-volatile RAM (NVRAM) (not shown), for storing basic routines that may help to start up the computing device 200 and to transfer information between the various components and devices. The read-only memory (ROM) 320 or NVRAM may also store other software components necessary for the operation of 200 and/or the system 300 in accordance with the aspects described herein.

The computing device 200 and/or the system 300 may operate in a networked environment using logical connections to remote computing nodes and computer systems of the communications network 310. The chipset 306 may include functionality for providing network connectivity through a network interface controller (NIC) 322. The network interface controller (NIC) 322 may be capable of connecting the computing device 200 and/or the system 300 to other computing nodes over the communications network 310. It should be appreciated that multiple implementations of the network interface controller (NIC) 322 may be present in the computing device 200 and/or the system 300, connecting the computing device to other types of networks and remote computer systems.

The network interface controller (NIC) 322 may be configured to implement a wired local area network technology, such as IEEE 802.3 ("Ethernet") or the like. The network interface controller (NIC) 322 may also comprise any suitable wireless network interface controller capable of wirelessly connecting and communicating with other devices or computing nodes on the communications network 310. For example, the network interface controller (NIC) 322 may operate in accordance with any of a variety of wireless communication protocols, including for example, the IEEE 802.11 ("Wi-Fi") protocol, the IEEE 802.16 or 802.20 ("WiMAX") protocols, the IEEE 802.15.4a ("Zigbee") protocol, the 802.15.3c ("UWB") protocol, and/or the like.

The computing device 200 and/or the system 300 may be connected to a mass storage device 328 that provides non-volatile storage (i.e., memory) for the computer. The mass storage device 328 may store system programs, application programs, other program modules, data, and/or the like and that may be related to implementation of the exemplary method for predicting a probability of cognitive impairment 100, which have been described in greater detail herein. The mass storage device 328 may be connected to the computing device 200 and/or the system 300 through a storage controller 324 connected to the chipset 306. The mass storage device 328 may consist of one or more physical storage units. A storage controller 324 may interface with the physical storage units through a serial attached SCSI (SAS) interface, a serial advanced technology attachment (SATA) interface, a fiber channel (FC) interface, or other type of interface for physically connecting and transferring data between computers and physical storage units.

The computing device 200 and/or the system 300 may store data on a mass storage device 328 by transforming the physical state of the physical storage units to reflect the information being stored. The specific transformation of a physical state may depend on various factors and on different implementations of this description. Examples of such factors may include, but are not limited to, the technology used to implement the physical storage units and whether the mass storage device 328 is characterized as primary or secondary storage and the like.

For example, the computing device 200 and/or the system 300 may store information to the mass storage device 328 by issuing instructions through a storage controller 324 to alter the magnetic characteristics of a particular location within a magnetic disk drive unit, the reflective or refractive characteristics of a particular location in an optical storage unit, or the electrical characteristics of a particular capacitor, transistor, or other discrete component in a solid-state storage unit. Other transformations of physical media are possible without departing from the scope and spirit of the present description, with the foregoing examples provided only to facilitate this description. The computing device 200 and/or the system 300 may read information from the mass storage device 328 by detecting the physical states or characteristics of one or more particular locations within the physical storage units.

In addition to the mass storage device 328 described herein, the computing device 200 and/or the system 300 may have access to other computer-readable storage media to store and retrieve information, such as program modules, data structures, or other data. It should be appreciated by those skilled in the art that computer-readable storage media may be any available media that provides for the storage of non-transitory data and that may be accessed by the computing device 200 and/or the system 300.

By way of example and not limitation, computer-readable storage media may include volatile and non-volatile, non-transitory computer-readable storage media, and removable and non-removable media implemented in any method or technology. However, as used herein, the term computer-readable storage media does not encompass transitory computer-readable storage media, such as signals. Computer-readable storage media includes, but is not limited to, RAM, ROM, erasable programmable ROM ("EPROM"), electrically erasable programmable ROM ("EEPROM"), flash memory or other solid-state memory technology, compact disc ROM ("CD-ROM"), digital versatile disk ("DVD"), high definition DVD ("HD-DVD"), BLU-RAY, or other optical storage, magnetic cassettes, magnetic tape, magnetic disk storage, other magnetic storage devices, or any other non-transitory medium that may be used to store the desired information in a non-transitory fashion.

A mass storage device, such as the mass storage device 328 depicted in FIG. 4, may store an operating system utilized to control the operation of the computing device 200 and/or the system 300. The operating system may comprise a version of the LINUX operating system. The operating system may comprise a version of the WINDOWS SERVER operating system from the MICROSOFT Corporation. According to additional aspects, the operating system may comprise a version of the UNIX operating system. Various mobile phone operating systems, such as IOS and ANDROID, may also be utilized. It should be appreciated that other operating systems may also be utilized. The mass storage device 328 may store other system or application programs and data utilized by the computing device 200.

The mass storage device 328 or other computer-readable storage media may also be encoded with computer-executable instructions, which, when loaded into the computing device 200, transforms the computing device from a general-purpose computing system into a special-purpose computer capable of implementing the aspects described herein. These computer-executable instructions transform the computing device 200 by specifying how the CPU(s) 304 transition between states, as described herein. The computing device 200 may have access to computer-readable storage media storing computer-executable instructions, which, when executed by the computing device 200, may perform the methods described in relation to FIG. 1.

A computing device, such as the computing device 200 and/or the system 300, may also include an input/output controller 332 for receiving and processing input from a number of input devices, such as a keyboard, a mouse, a touchpad, a touch screen, an electronic stylus, or other type of input device. Similarly, an input/output controller 332 may provide output to a display, such as a computer monitor, a flat-panel display, a digital projector, a printer, a plotter, or other type of output device. It will be appreciated that the computing device 200 may not include all of the components shown in FIG. 4, may include other components that are not explicitly shown in FIG. 4, or may utilize an architecture completely different than that shown in FIG. 4.

As described herein, a computing device may be a physical computing device, such as the computing device 200 and/or the system 300 of FIG. 4. A computing device may also include a virtual machine host process and one or more virtual machine instances. Computer-executable instructions may be executed by the physical hardware of a computing device indirectly through interpretation and/or execution of instructions stored and executed in the context of a virtual machine.

Accordingly, the disclosure has set forth implementations of the exemplary method for predicting a probability of cognitive impairment 100, the computing device 200, and/or the system 300 providing improved tools for assessing cognitive function in adults that integrates the depth of cognitive neuropsychological research and data available to clinicians while also providing an interface that is easily accessible to patients.

The following are a number of nonlimiting EXAMPLES of aspects of the disclosure.

One EXAMPLE includes: a computer-implemented method that includes generating a first set of objects and a second set of objects with a computing device. The computer-implemented method in addition includes displaying with the computing device the first set of objects to the patient individually, each for a period of time. The computer-implemented method moreover includes after all items in the first set have been presented, displaying with the computing device a first object belonging to either the first set of objects or the second set of objects. The computer-implemented method also includes receiving with the computing device a first response of whether the first object belongs to the first set of objects or the second set of objects. The computer-implemented method further includes determining with the computing device whether the first response correctly identifies a set of objects to which the first object belongs. The computer-implemented method in addition includes displaying with the computing device a second object from either the first set of objects or the second set of objects. The computer-implemented method moreover includes receiving with the computing device a second response of whether the first object belongs to the first set of objects or the second set of objects. The computer-implemented method also includes determining with the computing device whether the second response correctly identifies the set of objects to which the second object belongs. The computer-implemented method further includes applying with the computing device an algorithm to determine a probability of a cognitive characteristic based on a number of correct responses. The computer-implemented method in addition includes outputting with the computing device the probability of the cognitive characteristic.

The above-noted EXAMPLE may further include any one or a combination of more than one of the following EXAMPLES: The computer-implemented method of the above-noted EXAMPLE may include iteratively performing the steps of displaying an object and receiving a response until each object in the first set of objects and each object in the second set of objects has been displayed and the response has been received. The computer-implemented method of the above-noted EXAMPLE where the objects are images. The computer-implemented method of the above-noted EXAMPLE where the objects are words. The computer-implemented method of the above-noted EXAMPLE where the algorithm is a machine learning algorithm trained by processing a plurality of training responses to identify the cognitive characteristic. The computer-implemented method of the above-noted EXAMPLE where the algorithm is a heuristic algorithm. The computer-implemented method of the above-noted EXAMPLE where the cognitive characteristic is at least one of cognitive impairment, patient's sleep, mood, stress levels, or whether the patient speaks English as a second language. The computer-implemented method of the above-noted EXAMPLE where the computing device may include at least one of the following: a smartphone, a server computer, a workstation, an access point, a tablet computer, a laptop computer, a notebook computer, a desktop computer, a personal computer, a virtual reality (VR) device, and/or a wearable device. The computer-implemented method of the above-noted EXAMPLE where the outputting with the computing device the probability of the cognitive characteristic may include outputting to an electronic medical record (EMR) system.

One EXAMPLE includes: a device that includes instructions for generating a first set of objects and a second set of objects with a computing device. The device in addition includes instructions for displaying with the computing device the first set of objects to the patient individually, each for a period of time. The device moreover includes instructions for after all items in the first set have been presented, displaying with the computing device a first object belonging to either the first set of objects or the second set of objects. The device also includes instructions for receiving with the computing device a first response of whether the first object belongs to the first set of objects or the second set of objects. The device further includes instructions for determining with the computing device whether the first response correctly identifies a set of objects to which the first object belongs. The device in addition includes instructions for displaying with the computing device a second object from either the first set of objects or the second set of objects. The device moreover includes instructions for receiving with the computing device a second response of whether the first object belongs to the first set of objects or the second set of objects. The device also includes instructions for determining with the computing device whether the second response correctly identifies the set of objects to which the second object belongs. The device further includes instructions for applying with the computing device an algorithm to determine a probability of a cognitive characteristic based on a number of correct responses. The device in addition includes instructions for outputting with the computing device the probability of the cognitive characteristic.

The above-noted EXAMPLE may further include any one or a combination of more than one of the following EXAMPLES: The device of the above-noted EXAMPLE may include iteratively performing the steps of displaying an object and receiving a response until each object in the first set of objects and each object in the second set of objects has been displayed and the response has been received. The device of the above-noted EXAMPLE where the objects are images. The device of the above-noted EXAMPLE where the objects are words. The device of the above-noted EXAMPLE where the algorithm is a machine learning algorithm trained by processing a plurality of training responses to identify the cognitive characteristic. The device of the above-noted EXAMPLE where the algorithm is a heuristic algorithm. The device of the above-noted EXAMPLE where the cognitive characteristic is at least one of cognitive impairment, patient's sleep, mood, stress levels, or whether the patient speaks English as a second language. The device of the above-noted EXAMPLE where the computing device may include at least one of the following: a smartphone, a server computer, a workstation, an access point, a tablet computer, a laptop computer, a notebook computer, a desktop computer, a personal computer, a virtual reality (VR) device, and/or a wearable device. The device of the above-noted EXAMPLE where the outputting with the computing device the probability of the cognitive characteristic may include outputting to an electronic medical record (EMR) system.

One EXAMPLE includes: a computing device that includes at least one processor configured to generate a first set of objects and a second set of objects. The computing device in addition includes the at least one processor configured to display on a display device the first set of objects to the patient individually, each for a period of time. The computing device moreover includes the at least one processor configured to, after all items in the first set have been presented, display on the display device a first object belonging to either the first set of objects or the second set of objects. The computing device also includes the at least one processor configured to receive a first response of whether the first object belongs to the first set of objects or the second set of objects. The computing device further includes the at least one processor configured to determine whether the first response correctly identifies a set of objects to which the first object belongs. The computing device in addition includes the at least one processor configured to display on the display device a second object from either the first set of objects or the second set of objects. The computing device moreover includes the at least one processor configured to receive a second response of whether the first object belongs to the first set of objects or the second set of objects. The computing device also includes the at least one processor configured to determine whether the second response correctly identifies the set of objects to which the second object belongs. The computing device further includes the at least one processor configured to implement an algorithm to determine a probability of a cognitive characteristic based on a number of correct responses. The computing device in addition includes the at least one processor configured to output the probability of the cognitive characteristic.

The above-noted EXAMPLE may further include any one or a combination of more than one of the following EXAMPLES: The computing device of the above-noted EXAMPLE where the at least one processor is further configured to display an object and receive a response until each object in the first set of objects and each object in the second set of objects has been displayed and the response has been received. The computing device of the above-noted EXAMPLE where the objects are images. The computing device of the above-noted EXAMPLE where the objects are words. The computing device of the above-noted EXAMPLE where the algorithm is a machine learning algorithm trained by processing a plurality of training responses to identify the cognitive characteristic. The computing device of the above-noted EXAMPLE where the algorithm is a heuristic algorithm. The computing device of the above-noted EXAMPLE where the cognitive characteristic is at least one of cognitive impairment, patient's sleep, mood, stress levels, or whether the patient speaks English as a second language. The computing device of the above-noted EXAMPLE where the computing device may include at least one of the following: a smartphone, a server computer, a workstation, an access point, a tablet computer, a laptop computer, a notebook computer, a desktop computer, a personal computer, a virtual reality (VR) device, and/or a wearable device. The computing device of the above-noted EXAMPLE where the least one processor is further configured to output the probability of the cognitive characteristic to an electronic medical record (EMR) system.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Aspects of the disclosure may include communication channels that may be any type of wired or wireless electronic communications network, such as, e.g., a wired/wireless local area network (LAN), a wired/wireless personal area network (PAN), a wired/wireless home area network (HAN), a wired/wireless wide area network (WAN), a campus network, a metropolitan network, an enterprise private network, a virtual private network (VPN), an internetwork, a backbone network (BBN), a global area network (GAN), the Internet, an intranet, an extranet, an overlay network, Near field communication (NFC), a cellular telephone network, a Personal Communications Service (PCS), using known protocols such as the Global System for Mobile Communications (GSM), CDMA (Code-Division Multiple Access), GSM/EDGE and UMTS/HSPA network technologies, Long Term Evolution (LTE), 5G (5th generation mobile networks or 5th generation wireless systems), WiMAX, HSPA+, W-CDMA (Wideband Code-Division Multiple Access), CDMA2000 (also known as C2K or IMT Multi-Carrier (IMT-MC)), Wireless Fidelity (Wi-Fi), Bluetooth, and/or the like, and/or a combination of two or more thereof. The NFC standards cover communications protocols and data exchange formats, and are based on existing radio-frequency identification (RFID) standards including ISO/IEC 14443 and FeliCa. The standards include ISO/IEC 18092[3] and those defined by the NFC Forum The disclosure may be implemented in any type of computing devices, such as, e.g., a desktop computer, personal computer, a laptop/mobile computer, a personal data assistant (PDA), a mobile phone, a tablet computer, cloud computing device, and the like, with wired/wireless communications capabilities via the communication channels.

In an aspect, the exemplary method for predicting a probability of cognitive impairment 100 may be web-based. For example, a server may operate a web application to allow the exemplary method for predicting a probability of cognitive impairment 100 to operate in conjunction with a database. The web application implementation of the exemplary method for predicting a probability of cognitive impairment 100 may be hosted in a browser-controlled environment (e.g., a Java applet and/or the like), coded in a browser-supported language (e.g., JavaScript combined with a browser-rendered markup language (e.g., Hyper Text Markup Language (HTML) and/or the like)) and/or the like such that any computer running a common web browser (e.g., Internet Explorer™, Firefox™, Chrome™, Safari™ or the like) may render the application executable. A web-based service may be more beneficial due to the ubiquity of web browsers and the convenience of using a web browser as a client (i.e., thin client). Further, with inherent support for cross-platform compatibility, the web application may be maintained and updated without distributing and installing software on each.

In an aspect, the disclosure may be implemented in any type of mobile smartphones that are operated by any type of advanced mobile data processing and communication operating system, such as, e.g., an Apple™ iOS™ operating system, a Google™ Android™ operating system, a RIM™ Blackberry™ operating system, a Nokia™ Symbian™ operating system, a Microsoft™ Windows Mobile™ operating system, a Microsoft™ Windows Phone™ operating system, a Linux™ operating system or the like.

Further in accordance with various aspects of the disclosure, the methods including the exemplary method for predicting a probability of cognitive impairment 100 described herein are intended for operation with dedicated hardware implementations including, but not limited to, PCs, PDAs, semiconductors, application specific integrated circuits (ASIC), programmable logic arrays, cloud computing devices, and other hardware devices constructed to implement the methods described herein.

It should also be noted that the software implementations of the disclosure as described herein are optionally stored on a tangible storage medium, such as: a magnetic medium such as a disk or tape; a magneto-optical or optical medium such as a disk; or a solid state medium such as a memory card or other package that houses one or more read-only (non-volatile) memories, random access memories, or other re-writable (volatile) memories. A digital file attachment to email or other self-contained information archive or set of archives is considered a distribution medium equivalent to a tangible storage medium. Accordingly, the disclosure is considered to include a tangible storage medium or distribution medium, as listed herein and including art-recognized equivalents and successor media, in which the software implementations herein are stored.

Additionally, the various aspects of the disclosure may be implemented in a non-generic computer implementation. Moreover, the various aspects of the disclosure set forth herein improve the functioning of the system as is apparent from the disclosure hereof. Furthermore, the various aspects of the disclosure involve computer hardware that it specifically programmed to solve the complex problem addressed by the disclosure. Accordingly, the various aspects of the disclosure improve the functioning of the system overall in its specific implementation to perform the process set forth by the disclosure and as defined by the claims.

Aspects of the disclosure may be implemented in any type of computing devices, such as, e.g., a desktop computer, personal computer, a laptop/mobile computer, a personal data assistant (PDA), a mobile phone, a tablet computer, cloud computing device, and the like, with wired/wireless communications capabilities via the communication channels.

The artificial intelligence and/or machine learning implemented by the exemplary method for predicting a probability of cognitive impairment 100 may utilize any number of approaches including one or more of cybernetics and brain simulation, symbolic, cognitive simulation, logic-based, anti-logic, knowledge-based, sub-symbolic, embodied intelligence, computational intelligence and soft computing, machine learning and statistics, and the like.

Aspects of the disclosure may include a server executing an instance of an application or software configured to accept requests from a client and giving responses accordingly. The server may run on any computer including dedicated computers. The computer may include at least one processing element, typically a central processing unit (CPU), and some form of memory. The processing element may carry out arithmetic and logic operations, and a sequencing and control unit may change the order of operations in response to stored information. The server may include peripheral devices that may allow information to be retrieved from an external source, and the result of operations saved and retrieved. The server may operate within a client-server architecture. The server may perform some tasks on behalf of clients. The clients may connect to the server through the network on a communication channel as defined herein. The server may use memory with error detection and correction, redundant disks, redundant power supplies and so on.

Voice recognition software may be utilized in various aspects of the systems and methods. Users may be able to vocalize, rather than utilizing other input processes. For example, the voice recognition software may be configured for generating text from voice input from a microphone or other voice input. A speech signal processor may convert speech signals into digital data that can be processed by the processor. The processor may perform several distinct functions, including serving as the speech event analyzer, the dictation event subsystem, the text event subsystem, and the executor of the application program. The speech signal processor may generate speech event data and transmit this data to the processor to be processed first by the speech event analyzer. The speech event analyzer may generate a list or set of possible candidates among the system recordings that represent or match the voice input processed by the speech signal processor. The speech event analyzer may transmit the candidate sets to a dictation event subsystem. The dictation event subsystem may analyze the candidate sets and choose the best match candidate with the highest degree of similarity. This candidate is then considered the correct translation, and the dictation event subsystem forwards the translation to the text event subsystem which in turn inputs the translated text into the device.

The exemplary method for predicting a probability of cognitive impairment 100 may be implemented as an application and may be implemented to execute on an Apple™ iOS™ operating system, a Google™ Android™ operating system, a RIM™ Blackberry™ operating system, a Nokia™ Symbian™ operating system, a Microsoft™ Windows Mobile™ operating system, a Microsoft™ Windows Phone™ operating system, a Linux™ operating system or the like. The application may be displayed as an icon. The application may have been downloaded from the Internet, pre-installed, or the like. In some aspects, the application may be obtained from Google Play™, Android Market™, Apple Store™, or the like digital distribution source. The application may be written in conjunction with the software developers kit (SDK) associated with an Apple™ iOS™ operating system, a Google™ Android™ operating system, a RIM™ Blackberry™ operating system, a Nokia™ Symbian™ operating system, a Microsoft™ Windows Mobile™ operating system, a Microsoft™ Windows Phone™ operating system, a Linux™ operating system or the like.

The many features and advantages of the disclosure are apparent from the detailed specification, and, thus, it is intended by the appended claims to cover all such features and advantages of the disclosure which fall within the true spirit and scope of the disclosure. Further, since numerous modifications and variations will readily occur to those skilled in the art, it is not desired to limit the disclosure to the exact construction and operation illustrated and described, and, accordingly, all suitable modifications and equivalents may be resorted to that fall within the scope of the disclosure.

What is claimed is:

1. A computer-implemented method of determining a cognitive characteristic of a patient, the method comprising:
   generating a first set of objects and a second set of objects with a computing device;
   displaying on a display device in response to the computing device, the first set of objects to the patient individually, each for a period of time;
   after all items in the first set have been presented, displaying on the display device in response to the computing device a first object belonging to either the first set of objects or the second set of objects;
   receiving, using the computing device, a first response from the patient of whether the first object belongs to the first set of objects or the second set of objects;
   determining, using the computing device, whether the first response correctly identifies a set of objects to which the first object belongs;
   displaying on the display device in response to, the computing device, a second object from either the first set of objects or the second set of objects;
   receiving, using the computing device, a second response from the patient of whether the first object belongs to the first set of objects or the second set of objects;
   determining, using the computing device, whether the second response correctly identifies the set of objects to which the second object belongs;
   controlling with the computing device an implementation of a machine learning algorithm to determine a cognitive characteristic based on responses received from the patient, wherein the machine learning algorithm is trained by processing a plurality of patient responses to identify the cognitive characteristic; and
   outputting with the computing device a cognitive characteristic of the patient, wherein the outputted cognitive characteristic provides a clinician with information for aiding the clinician in clinical decision making.

2. The computer-implemented method of claim 1, further comprising iteratively performing the steps of displaying an object and receiving a response until each object in the first set of objects and each object in the second set of objects has been displayed and the response has been received.

3. The computer-implemented method of claim 1, wherein the objects are images.

4. The computer-implemented method of claim 1, wherein the objects are words.

5. The computer-implemented method of claim 1, wherein the machine learning algorithm is a heuristic algorithm.

6. The computer-implemented method of claim 1, wherein the cognitive characteristic is at least one of cognitive impairment, patient's sleep, mood, stress levels, or whether the patient speaks English as a second language.

7. The computer-implemented method of claim 1, wherein the computing device comprises at least one of the following: a smartphone, a server computer, a workstation, an access point, a tablet computer, a laptop computer, a notebook computer, a desktop computer, a personal computer, a virtual reality (VR) device, and/or a wearable device.

8. The computer-implemented method of claim 1, wherein the outputting with the computing device the cognitive characteristic comprises outputting to an electronic medical record (EMR) system.

9. A device configured for storing non-transitory instructions that are configured such that when the non-transitory instructions are executed by at least one processor, the at least one processor implements a method of determining a cognitive characteristic of a patient, the non-transitory instructions comprising:
generating a first set of objects and a second set of objects with a computing device;
displaying on a display device in response to the computing device, the first set of objects to the patient individually, each for a period of time;
after all items in the first set have been presented, displaying on a display device in response to the computing device a first object belonging to either the first set of objects or the second set of objects;
receiving, using the computing device a first response from the patient of whether the first object belongs to the first set of objects or the second set of objects;
determining, using the computing device whether the first response correctly identifies a set of objects to which the first object belongs;
displaying on a display device in response to the computing device, a second object from either the first set of objects or the second set of objects;
receiving, using the computing device, a second response from the patient of whether the first object belongs to the first set of objects or the second set of objects;
determining, using the computing device, whether the second response correctly identifies the set of objects to which the second object belongs;
controlling, with the computing device an implementation of a machine learning algorithm to determine a cognitive characteristic based on responses received from the patient, wherein the machine learning algorithm is trained by processing a plurality of patient responses; and
outputting with the computing device a cognitive characteristic of the patient, wherein the outputted cognitive characteristic provides a clinician with information for aiding the clinician in clinical decision making.

10. The device of claim 9, further comprising iteratively performing the steps of displaying an object and receiving a response until each object in the first set of objects and each object in the second set of objects has been displayed and the response has been received.

11. The device of claim 9, wherein the objects are images.

12. The device of claim 9, wherein the objects are words.

13. The device of claim 9, wherein the machine learning algorithm is a heuristic algorithm.

14. The device of claim 9, wherein the cognitive characteristic is at least one of cognitive impairment, patient's sleep, mood, stress levels, or whether the patient speaks English as a second language.

15. The device of claim 9, wherein the computing device comprises at least one of the following: a smartphone, a server computer, a workstation, an access point, a tablet computer, a laptop computer, a notebook computer, a desktop computer, a personal computer, a virtual reality (VR) device, and/or a wearable device.

16. The device of claim 9, wherein the outputting with the computing device the cognitive characteristic comprises outputting to an electronic medical record (EMR) system.

17. A computing device configured to determine a cognitive characteristic of a patient, the computing device comprising:
at least one processor configured to generate a first set of objects and a second set of objects;
the at least one processor configured to display on a display device the first set of objects to the patient individually, each for a period of time;
the at least one processor configured to, after all items in the first set have been presented, display on the display device a first object belonging to either the first set of objects or the second set of objects;
the at least one processor configured to receive a first response of whether the first object belongs to the first set of objects or the second set of objects;
the at least one processor configured to determine whether the first response correctly identifies a set of objects to which the first object belongs;
the at least one processor configured to display on the display device a second object from either the first set of objects or the second set of objects;
the at least one processor configured to receive a second response of whether the first object belongs to the first set of objects or the second set of objects;
the at least one processor configured to determine whether the second response correctly identifies the set of objects to which the second object belongs;
the at least one processor configured to implement a machine learning algorithm to determine a cognitive characteristic, based on responses received from the patient, wherein the machine learning algorithm is trained by processing a plurality of patient responses; and
the at least one processor configured to output a cognitive characteristic,
wherein the outputted cognitive characteristic provides a clinician with information for aiding the clinician in clinical decision making.

18. The computing device of claim 17, wherein the at least one processor is further configured to display an object and receive a response until each object in the first set of objects and each object in the second set of objects has been displayed and the response has been received.

19. The computing device of claim 17, wherein the objects are images.

20. The computing device of claim 17, wherein the objects are words.

21. The computing device of claim 17, wherein the machine learning algorithm is a heuristic algorithm.

22. The computing device of claim 17, wherein the cognitive characteristic is at least one of cognitive impairment, patient's sleep, mood, stress levels, or whether the patient speaks English as a second language.

23. The computing device of claim 17, wherein the computing device comprises at least one of the following: a smartphone, a server computer, a workstation, an access point, a tablet computer, a laptop computer, a notebook computer, a desktop computer, a personal computer, a virtual reality (VR) device, and/or a wearable device.

24. The computing device of claim 17, wherein the least one processor is further configured to output the cognitive characteristic to an electronic medical record (EMR) system.

* * * * *